United States Patent [19]

Velazquez

[11] Patent Number: 4,484,571
[45] Date of Patent: Nov. 27, 1984

[54] PATIENT SECURITY AND RESTRAINT SYSTEM
[75] Inventor: Herb F. Velazquez, Milwaukee, Wis.
[73] Assignee: General Electric Company, Milwaukee, Wis.
[21] Appl. No.: 454,933
[22] Filed: Jan. 3, 1983
[51] Int. Cl.³ ............................................. A61F 13/00
[52] U.S. Cl. ..................................... 128/134; 269/328
[58] Field of Search ................ 128/134, 133; 269/328

[56] References Cited

U.S. PATENT DOCUMENTS

| | | | |
|---|---|---|---|
| 2,743,974 | 5/1956 | Black | 269/328 |
| 2,912,977 | 11/1959 | Holbrook | 128/134 |
| 3,035,278 | 5/1962 | Golding | 269/328 X |
| 3,861,666 | 1/1975 | Nishiyama et al. | 128/134 X |
| 4,069,813 | 1/1978 | Gilula | 128/133 X |

Primary Examiner—John D. Yasko
Attorney, Agent, or Firm—Alexander M. Gerasimow; Douglas E. Stoner

[57] ABSTRACT

In one embodiment of the patient security and restraint system, a cradle for supporting a patient is provided with track edges which are configured as cylindrical channels communicating to the exterior by means of a slit-like aperture. Runners, to which the patient restraint straps are secured, are provided with rod-like portions which are captured in the cylindrical channels for longitudinal movement. In an alternative embodiment, the cylindrical channels are formed in the runners, while the rod-like portion is provided along the edges of the patient cradle.

6 Claims, 7 Drawing Figures

PATIENT SECURITY AND RESTRAINT SYSTEM

BACKGROUND OF THE INVENTION

This invention relates to a system for securing and restraining a patient undergoing examination by means of a medical diagnostic imaging device. More specifically, this invention relates to such a system for use with computerized tomography (CT) and nuclear magnetic resonance (NMR) imaging apparatus, for example.

In many medical diagnostic imaging procedures, it is frequently either necessary or desirable to secure and restrain a patient to the patient-supporting cradle. For example, it may be necessary to secure and restrain the patient to avoid accidental falls off the cradle. As will be more fully described hereinafter, it may also be necessary to secure and restrain the patient to minimize body motion during the imaging procedure. In the case of uncooperative patients, the security and restraint system additionally provides the means to control an otherwise combative patient.

One of the imaging procedures which requires the patient to remain motionless for a substantial length of time during the data-collecting process is NMR imaging. In NMR imaging, the data is collected by subjecting the patient to various magnetic fields and radio-frequency pulses. During the data acquisition period (which may extend for several minutes or longer), the patient must remain substantially motionless so that sufficient data is collected to reconstruct images which are free of motion-related artifacts. Another reason for the prolonged data collecting period is so that the signal-to-noise ratio of the collected data is within the required limits for obtaining good image quality. In computerized tomography, the problem of patient motion is less severe since, as is known, scan time is typically of the order of seconds. Nonetheless, for the reasons given hereinabove, it is desirable that the patient remain motionless during the scanning operation. In the computed projection radiography method, which employs the same apparatus as computerized tomography, the patient is advanced longitudinally through a fan-shaped X-ray beam at a constant velocity for undergoing a line-by-line scan. It will be appreciated, therefore, that during this procedure it is again desirable that the patient remain motionless so as to ensure high image quality.

It is important to note that the patient security and restraint system must be configured to comfortably accommodate patients of various sizes. The restraints must also be movable along the cradle so as to secure various parts of the body, such as arms, chest, knees, and ankles, as necessary. In order to esure prompt care of the patient in the event of an emergency, the restraints must be removable quickly and easily. For use in apparatus, such as computerized tomography utilizing ionizing radiation, the restraints must be substantially transmissive to the X-ray radiation. In NMR imaging, the materials must be non-ferromagnetic to avoid distrubing the homogeneity of the carefully controlled magnetic field needed for obtaining imaging information. It is, therefore, a principal object of the invention to provide a patient security and restraint system which satisfies the constraints described.

SUMMARY OF THE INVENTION

A medical diagnostic apparatus includes enlongate support means for supporting a patient and strap means having runners affixed thereto for restraining and securing a patient to the support means. A pair of elongate members is provided laterally along the elongated support and opposite one another. Each member is configured to cooperate with a complementarily shaped portion of the runner such that the position of the runner relative to the elongated support is slidably adjustable.

BRIEF DESCRIPTION OF THE DRAWINGS

The features of the invention believed to be novel are set forth with particularity in the appended claims. The invention itself, however, both as to its organization and method of operation, together with further objects and advantages thereof, may best be understood by reference to the following description taken in conjunction with the accompanying drawings in which:

DETAILED DESCRIPTION OF THE INVENTION

Figure 1:
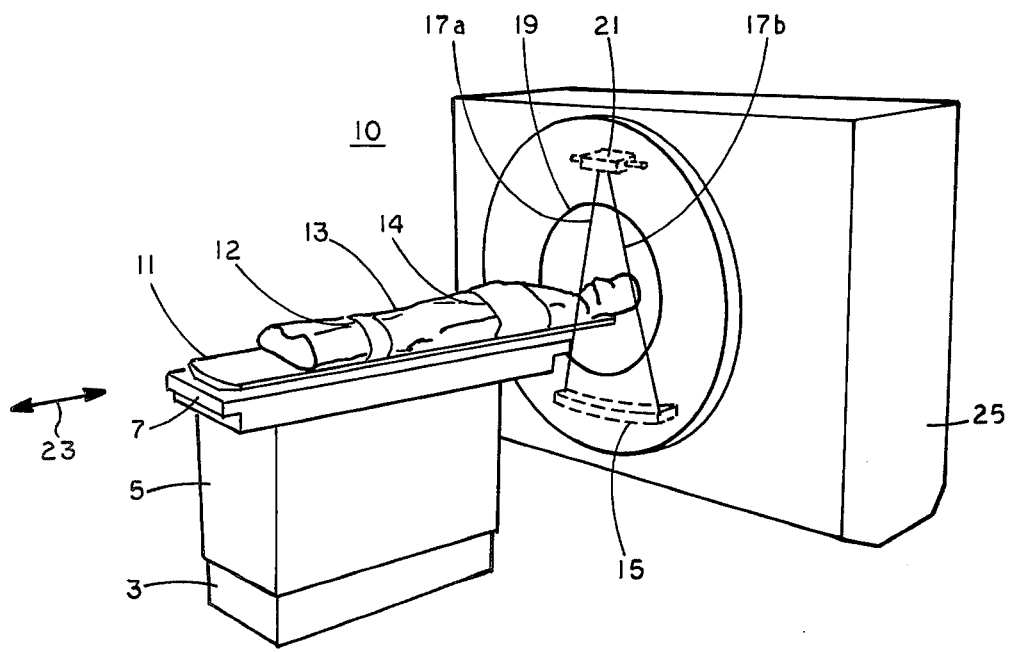
FIG. 1 is a perspective view of a typical computed tomography and computed projection radiography apparatus, together with the new patient security and restraint system.

An exemplary application of the new patient security and restraint system will be described wtih reference to FIG. 1 which illustrates a typical apparatus suitable for performing computed tomography and computed, or scanned, projection radiography. The apparatus is designated generally by numeral 10 and includes a housing 25 supported from within by a gantry, which is not visible in FIG. 1, but the details of which may be ascertained by reference to U.S. Pat. Nos. 4,112,303, and 4,115,695, both of which are assigned to the same assignee as the present invention, and both of which are incorporated herein by reference. The gantry is instrumental in tilting the housing from the vertical position when the apparatus is used as a computerized tomography scanner to image body sections at an angle. Essential components of the apparatus are an X-ray source 21 and a multicell X-ray detector 15. The source and detector are mounted on a scanner base, not visible, which is journalled for rotation so that the X-ray source and the detector can orbit jointly about the horizontal axis when a computed axial tomography scan is being performed. The apparatus has a circular opening 19 that is nominally centered on a horizontal axis 23 to provide a passageway for advancing and retracting a patient 13 supported by a patient cradle 11, relative to a fan-shaped X-ray beam whose boundaries are marked 17a and 17b.

As is known, when performing computed tomography, the patient is advanced longitudinally in steps so that successive transverse layers of the body may be scanned by joint orbiting of X-ray source 21 and detector array 15 while attenuation data is obtained from the detector for permitting reconstruction of an X-ray image in a vertical section of the body. When the apparatus is used for performing computed projection radiography, X-ray source 21 and detector 15 are locked against rotation, and the patient is advanced at a constant speed through the X-ray beam, since the cells in the X-ray detector that provide the attenuation data must be read out at constant timed intervals. In this manner, the computer, not shown, can relate the body position to the attenuation data and produce an image on a television screen, not shown, representative of a projection of the body that is essentially a shadowgraph.

The components of the X-ray table assembly are identified generally in FIG. 1 and are represented schematically. The apparatus includes a floor-mounted base 3 having mounted thereon an elevator portion 5 which is movable vertically with respect to the floor. A first carriage or intermediate support 7 is mounted on elevator portion 5 in a fashion that permits it to be moved longitudinally, that is, parallel to the axis of rotation 23 of the scanner, as well as in a vertical direction. A patient cradle 11, made substantially of X-ray-transmissive material, is mounted on intermediate support 7 for longitudinal movement in opposite directions relative thereto. The intermediate support and cradle are driven longitudinally in that order to advance patient 13 in the forward direction towards circular opening 19 in housing 25. They are driven in opposite order to move the patient rearwardly, that is, away from the housing.

Figure 2:
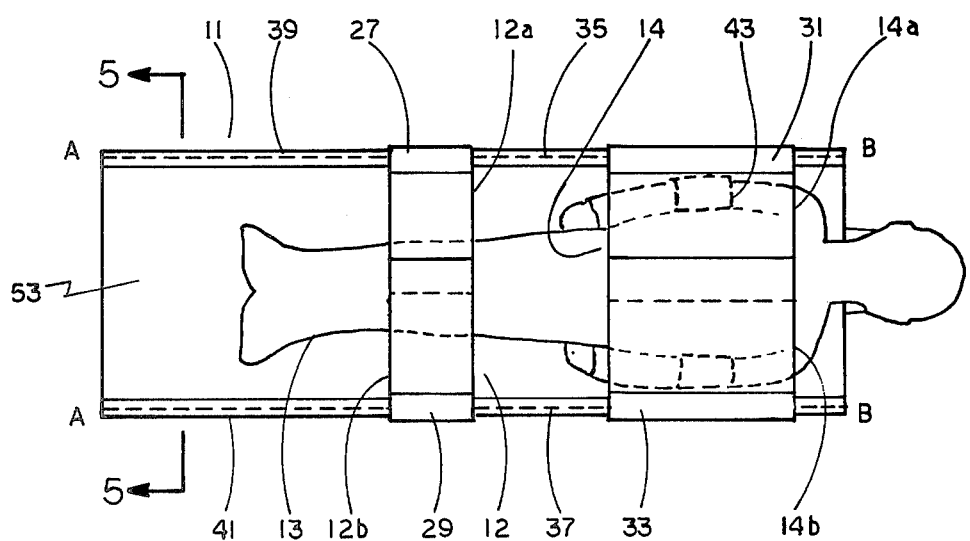
FIG. 2 is a plan view of the patient-supporting cradle and the security and restraint system.
Figure 3:
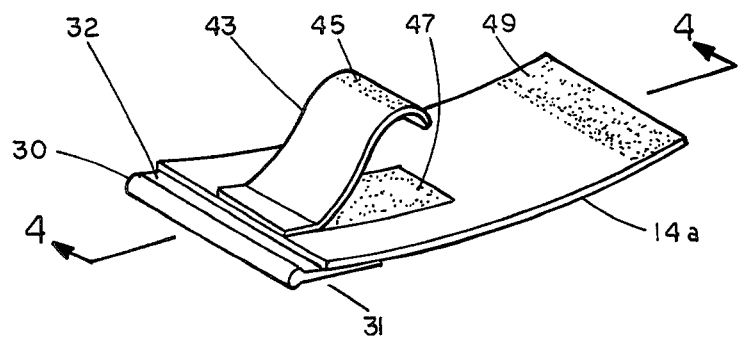
FIG. 3 is a perspective view of a runner having wrist and body straps attached thereto.
Figure 4:
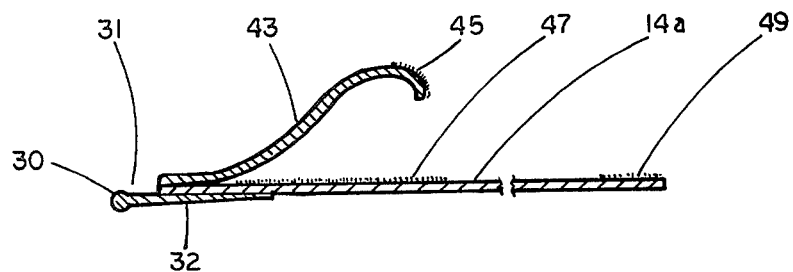
FIG. 4 is a sectional view of a runner having a strap attached thereto taken on a line 4—4 shown in FIG. 3.

The details of construction of the preferred emobodiment of the patient security and restraint system may be best understood if reference is made to FIG. 2 which depicts a plan view of cradle 11 on which patient 13 is held in place by means of a knee strap set 12 and a chest strap set 14. Strap sets 12 and 14 are each comprised of two sections 12a-12b and 14a-14b, respectively. At one end, the strap sections are secured to one another over the body of patient 13 by means of fasteners adapted for quickly releasing the straps and releasing the patient in the event of an emergency. Such fasteners may, for example, include non-metallic snaps, fastening tape, or, preferably, woven nylon loop-and-hook fasteners of the type known under the trade name VELCRO, and which are available commercially from Velcro, Inc., Manchester, New Hampshire. At the other end, the strap sections are attached to flexible vinyl runners 27, 29, 31, and 33, as best seen in FIGS. 3 and 4 which illustrate one section (e.g.,. 14a) of chest strap set 14. Referring again to FIG. 2, runners 27, 29, 31, and 33 are adapted to slide between points designated A and B on tracks 35 and 37 formed, respectively, in elongated members 39 and 41 which are secured to the edges of cradle 11. The free and easy movement of the runners on the tracks permits the position of straps 12 and 14 to be easily adjusted to effectively accommodate patients of varying heights. Patients of varying girths may be accommodated by adjusting the degree of overlap of strap sections 12a-12b and 14a-14b.

Although the description of the strap and runner will be with reference to runner 31, and strap section 14a, it should be noted that the construction of runners 27, 29, and 33 and straps 12a, 12b, and 14b is substantially indentical. FIGS. 3 and 4 are, respectively, perspective and sectional views of one chest-strap section, 14a, and the runner, 31, associated therewith. Runner 31 is made up of a rod-like portion 30 which tapers to a flexible lateral extension 32 to which a wide chest-strap section 14a and a narrow arm-strap section 43 are secured. Arm strap 43 is provided with woven nylon hooks (or loops) 45 which, when pressed together, attach to loops (or hooks) 47 provided in chest strap 14a. Similarly, chest strap 14a is provided with woven nylon hooks (for example) 49 which attach to woven nylon loops (not shown) on chest-strap section 14b.

Figure 5:
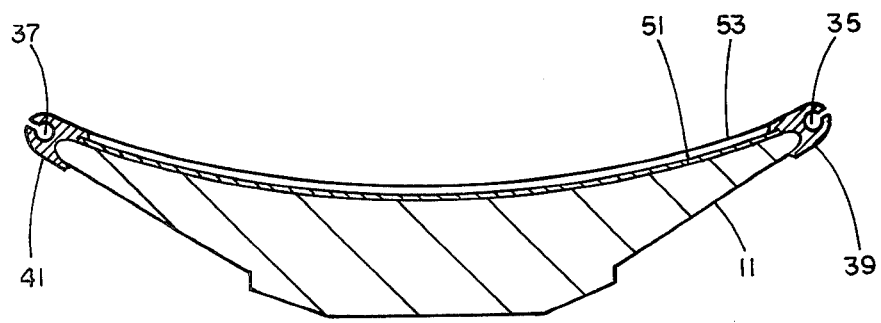
FIG. 5 is a cross section through the cradle and the security and restraint system taken on a line corresponding with 5—5 in FIG. 2.

FIG. 5 is a cross-sectional view of cradle 11 and the new patient security and restraint system taken along line 5—5 in FIG. 2. Elongate members 39 and 41 are each provided with a concave groove which fits over complementarily shaped convex edge of cradle 11. Members 39 and 41 are held in place by a planar sheet 51 which is shaped so as to conform to the contour of the cradle and which is cemented to each of members 39 and 41 to form an integral assembly. In use, planar sheet 51 is held in place by the weight of the patient, or, if desired, planar sheet 51 may be cemented in place. To add to the comfort of the patient, a cushion 53 may be provided over sheet 51. Each of members 39 and 41 is provided with tracks 35 and 37, respectively, configured as cylindrical channels which are sized to accommodate rod-like portion 30 of runner 31. The channels communicate to the outside along the length of members 39 and 41 through a slit-like aperture sized to accommodate tapered portion 32 of runner 31 (FIG. 4). Straps 12a and 14b may be inserted into a channel 35, for example, by aligning the longitudinal axis of rod-like member 30 with that of the channel and by aligning runner extension 32 of runner 31 with the slit-like aperture and sliding the runner on by moving it laterally. It will be apparent that in this manner new straps, or different size straps may be easily and quickly inserted.

Figure 6:
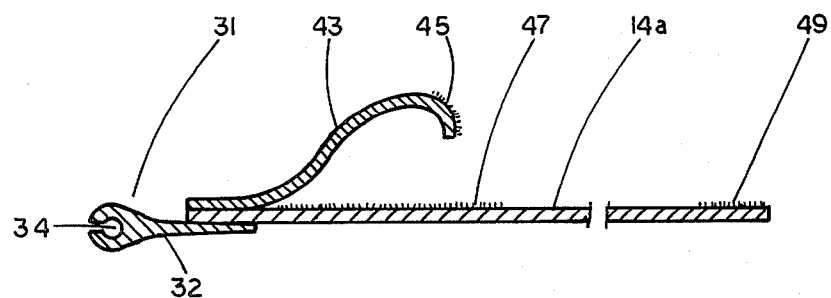
FIG. 6 is a sectional view of the patient-supporting cradle showing an alternative embodiment of the patient security and restraint system.
Figure 7:
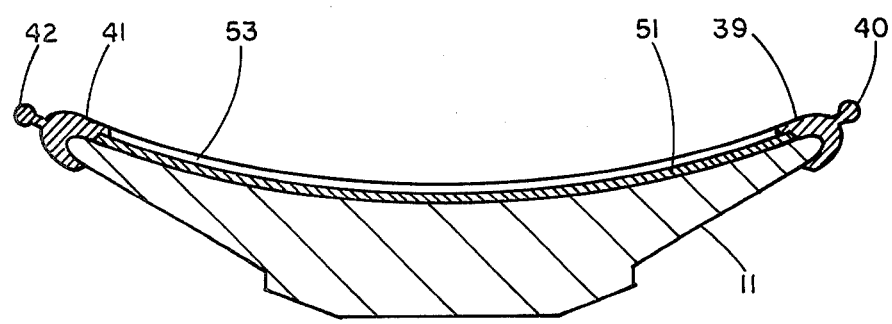
FIG. 7 is a sectional view of an alternative embodiment of a runner which is useful with the embodiment depicted in FIG. 6.

An alternative embodiment of the runners and the elongated members with which the runners cooperate to attach the straps to the cradle is depicted in FIGS. 6 and 7 in which like parts are assigned the same reference numerals as in FIGS. 4 and 5. This embodiment is substantially identical to that described hereinbefore with the notable exception that a cylindrial channel 34 is now provided in runner 31, for example, while the rod-like member 40, sized to fit into channel 34, is provided along the length of each of members 39 and 41.

Although the new patient security and restraint system has been described with reference to a computed tomography imaging apparatus, it will be appreciated the system is useful with other apparatus (such as ultrasound scanners and nuclear diagnostic devices which include gamma cameras and nuclear scanners) where it is advantageous to secure and restrain the patient. Another example of such an apparatus is a nuclear magnetic resonance imaging scanner. In the case of apparatus utilizing ionizing radiation to scan the patient, the cradle and the patient restraint system is made from materials selected to be substantially transparent to the radiation. In the case of NMR imaging apparatus, the materials are selected to be substantially inert to NMR excitation, electrically non-conductive and substantially non-ferromagnetic. In the preferred embodiment, the cradle is a molded resin product, while elongated members 39 and 41 and planar sheet 11 are extruded and formed, respectively, from suitable engineering plastic materials, such as ABS, which is a polymer manufactured from acrylonitrile, butadiene, and styrene monomers.

While this invention has been described with reference to particular embodiments and examples, other modifications and variations will occur to those skilled in the art in view of the above teachings. Accordingly, it should be understood that within the scope of the appended claims the invention may be practiced otherwise than is specifically described.

The invention claimed is:

1. In a medical diagnostic apparatus including:
   elongated support means for supporting a patient;
   strap means for restraining and securing the patient to said support means;
   runner means secured to said strap means; and
   track means co-extensive with at least a portion of said support means and disposed laterally along each edge of said support means, said track means being configured to cooperate with a complementarily shaped portion of said runner means, such that the position of said runner means relative to said support means is slidably adjustable;
   the improvement wherein said track means and runner means comprise, respectively:
   a pair of elongated members, one of said members being disposed laterally along one edge of said support means, the other one of said members being spaced from said one member and disposed laterally along the other edge of said support means, each of said elongated members having a longitudinal, substantially cylindrical channel formed therein, said channel communicating to the exterior by means of a slit-like aperture formed in said elongated member; and
   said runner means having a rod-like portion and a tapered portion extending laterally from said rod-like portion, at least one of said runner means being captured within said cylindrical channel in each of said elongated means by means of said rod-like portion such that said tapered portion passes through said slit-like aperture, said runner means being thus enabled for longitudinal movement along said elongated member.

2. The apparatus of claim 1 further comprising a planar member positioned on said support means and configured to conform to the contour of said support means, said planar member being secured to each of said elongate members along the length thereof to form an integral assembly.

3. In a medical diagnostic apparatus including:
   elongated support means for supporting a patient;
   strap means for restraining and securing the patient to said support means;
   runner means secured to said strap means; and
   track means co-extensive with at least a portion of said support means and disposed laterally along each edge of said support means, said track means being configured to cooperate with a complementarily shaped portion of said runner means, such that the position of said runner means relative to said support means is slidably adjustable;
   the improvement wherein said track means and said runner means comprise, respectively:
   a pair of elongated members, one of said members being disposed laterally along one edge of said support means, the other one of said members being spaced from said one member and disposed laterally along the other edge of said support means, each of said elongated members having along the length thereof a rod-like member connected thereto by a narrow connecting member; and
   said runner means having a substantially cylindrical channel formed therein, said channel communicating to the exterior by means of a slit-like aperture, at least one of said runner means being enabled for a longitudinal movement along each of said elongated members by means of said rod-like members being captured with cylindrical channels in a corresponding one of said runner means, such that said narrow connecting member passes through said slit-like aperture.

4. The apparatus of claim 3 further comprising a planar member positioned on said support means and configured to conform to the contour of said support means, said planar member being secured to each of said elongate members along the length thereof to form an integral assembly.

5. In a medical diagnostic apparatus, including:
   elongated support means for supporting a patient;
   strap means for restraining and securing the patient to said support means;
   runner means secured to said strap means;
   the improvement wherein said elongated support means is provided along each of the lateral edges thereof with a channel, which channel communicates to the exterior by means of slit-like aperture formed in said elongate support means; and
   said runner means having an enlarged portion and a tapered portion extending laterally from said enlarged portion, at least one of said runner means being captured within each channel in said elongated support means by means of said enlarged portion such that said tapered portion passes through said slit-like aperture, said runner means being thus enabled for longitudinal movement along said elongated member.

6. In a medical diagnostic apparatus, including:
   elongated support means for supporting a patient;
   strap means for restraining and securing the patient to said support means;
   runner means secured to said strap means;
   the improvement wherein said elongated support means is provided along each of the lateral edges thereof with an enlarged member connected thereto by a narrow connecting member; and
   said runner means having a channel formed therein, said channel communicating to the exterior by means of a slit-like aperture and being configured to slidably receive said enlarged member such that said narrow member passes through said slit-like aperture, said runner means being thus enabled for longitudinal movement along the lateral edges of said elongated support means.

* * * * *

UNITED STATES PATENT AND TRADEMARK OFFICE
CERTIFICATE OF CORRECTION

PATENT NO. : 4,484,571

DATED : Nov. 27, 1984

INVENTOR(S) : Herb F. Velazquez

It is certified that error appears in the above-identified patent and that said Letters Patent is hereby corrected as shown below:

Column 1, line 60 change "distrubing" to --disturbing--;
Column 1, line 67 change "enlongate" to --elongate--.
Column 3, lines 34 and 35, change "emobodiment" to --embodiment--;
Column 3, lines 66 and 67, change "indentical" to --identical--.
Column 4, line 43, change "cylindrial" to --cylindrical--.
Column 6, Line 17, change "with" to --within--.

Signed and Sealed this

Twenty-first Day of May 1985

[SEAL]

Attest:

DONALD J. QUIGG

Attesting Officer   Acting Commissioner of Patents and Trademarks